United States Patent [19]

Adolph et al.

[11] 3,973,123
[45] Aug. 3, 1976

[54] MEASURING TRANSPARENCY OF GASES, PARTICULARLY THE OPTICAL TRANSMISSION OF INTERNAL COMBUSTION ENGINE EXHAUST GASES

[75] Inventors: Dietrich Adolph, Ebersbach, Fils; Walter Dinkelacker, Stuttgart, both of Germany

[73] Assignee: Robert Bosch G.m.b.H., Stuttgart, Germany

[22] Filed: May 21, 1975

[21] Appl. No.: 579,463

[30] Foreign Application Priority Data
May 28, 1974 Germany............................ 2425876
Mar. 21, 1975 Germany............................ 2512538

[52] U.S. Cl.................................. 250/343; 356/207
[51] Int. Cl.² ......................................... G01J 1/00
[58] Field of Search ........... 250/343, 345, 344, 352; 356/207

[56] References Cited
UNITED STATES PATENTS

| | | | |
|---|---|---|---|
| 2,901,626 | 8/1959 | Becker............................. | 250/343 |
| 3,519,356 | 7/1970 | Kroeger et al..................... | 356/207 |
| 3,581,085 | 5/1971 | Barrett............................. | 250/365 |
| 3,609,382 | 9/1971 | Moore et al. ..................... | 356/207 |
| 3,628,873 | 12/1971 | Leitz................................ | 250/574 |
| 3,790,289 | 2/1974 | Schmidt............................ | 356/207 |
| 3,826,918 | 7/1974 | Koogle et al....................... | 250/343 |
| 3,867,640 | 2/1975 | Paulsen............................ | 356/207 |

*Primary Examiner*—Harold A. Dixon
*Assistant Examiner*—Bruce C. Anderson
*Attorney, Agent, or Firm*—Flynn and Frishauf

[57] ABSTRACT

To prevent contamination of confining surfaces of vessels through which a light beam is passed, the attenuation of which is a measure of the optical transparency of exhaust gases from Diesel engines, transparent disks, such as glass disks, are rotated adjacent the chamber and heated, for example by gas jets or an infrared source to such a temperature that the disk temperature is raised to a level sufficient to burn off any residual deposits left by the gases on the disks, so that the transparency of the disk will not be impaired and adulterate the measuring results.

17 Claims, 3 Drawing Figures

MEASURING TRANSPARENCY OF GASES, PARTICULARLY THE OPTICAL TRANSMISSION OF INTERNAL COMBUSTION ENGINE EXHAUST GASES

The present invention relates to an apparatus to measure a characteristic of gases, and more particularly to measure the transparency of gases which are emitted as exhaust from internal combustion engines, especially from Diesel engines. The apparatus, in accordance with the invention, measures the intensity of a light beam which is guided through a chamber filled with the gases which are to be analyzed, the chamber being defined at the inlet side and outlet side of the light beam by transparent panes.

Components or elements contained in the exhaust gases of internal combustion engines, particularly Diesel engines, can be analyzed by measuring the transparency of the gas being emitted from the engine to the passage of a beam of light. Such apparatus usually utilize a beam of light which is transmitted through a measuring chamber to illluminate a photo cell which provides a signal representative of the attenuation of light when the light passes through the gas, rather than through clear air. Solid particles, particularly carbon and soot particles contained in gases emitted from internal combustion engines are usually the cause of change in transmissivity of the gas to light; such particles, however, deposit on the walls of the chamber, or on the surface of the light source and on the photo cell. The measuring result becomes inaccurate, or impossible, unless both the light source and the photo cells are frefquently cleaned.

It has previously been proposed to prevent contamination of the light source and the photo cell by blowing a stream of clean air transverse to the stream of the gases to be measured by means of a ventilator contained in a separate housing, thereby spacing the light source and the photo cell from the contaminating gases. Such a stream of air is intended to deflect the gases from the surfaces of the light source and the photo cell, or their housings, respectively, and thus keep the surfaces of the light-emitting and light-sensitive elements clean and of uniform light transmissivity. The surfaces of the photo cell and the light source will, however, become contaminated even if such a stream of clean air is blown thereacross. Further, the additonal air being introduced influences the result of the test, and the length of the measuring gas column which receives the test result is also dependent to some extent on the stream of clean air, which additionally changes the measuring result from the true value. The air supply characteristics of the blower for clean air also influence the test result, so that inaccuracies which are difficult to evaluate, or to compensate, may be introduced.

It has previously been proposed to close off the measuring chamber for exhaust gases of an internal combustion engine by means of a rotating disk; the disk is passed by a cleaning or wiper arrangement which is intended to remove contaminating particles from the surfaces of the disk (see, for example, German DT-GM 1,980,419). Such an arrangement requires a complicated construction and additionally uses a polishing substance to clean the disk; the extent of application of the cleaning or polishing substance influences the light transmissivity through the disk. Such an arrangement can be used only for a comparatively short duration of measurement; using such an apparatus for a longer period of time, or for a large number of sequential tests, causes contamination and soiling of the cleaning device itself, so that eventually the disk is not sufficiently cleaned. Abrasive particles which get caught in the cleaning apparatus leave scratch marks on the disk.

It is an object of the present invention to provide a gas transmissivity measuring apparatus which is so constructed that contaminating particles can be readily removed from panes confining the measuring chamber, so that contaminating deposits on these panes will not influence the measuring result.

SUBJECT MATTER OF THE PRESENT INVENTION

Briefly, at least one heating means, such as a burner, an infrared source or the like, is located with respect to the panes such that particles which deposit on the panes are burned off.

The invention will be described by way of example with reference to the accompanying drawings, wherein.

Figure 1:
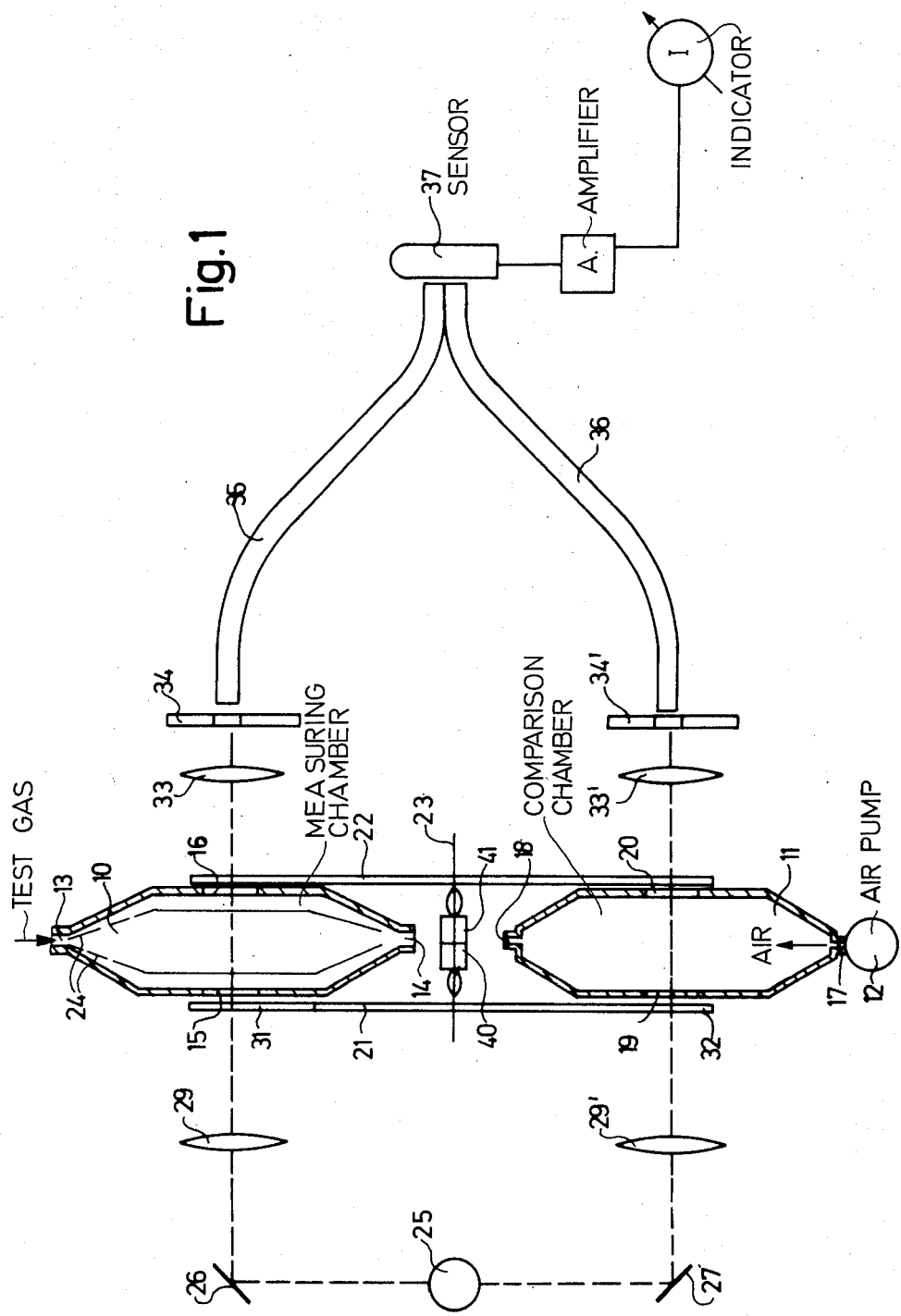
FIG. 1 is a highly schematic view of one embodiment of a construction of a measuring apparatus to determine the light transmissivity of gases.

Two chambers 10 and 11 (Fig. 1) are provided, in which chamber 10 is the measuring chamber and chamber 11 is a comparison chamber. The gas to be measured is introduced into chamber 10; a typical gas is the exhaust from Diesel engines, the exhaust being conducted through the chamber 10 to flow therethrough. The comparison chamber 11 is connected to a pump 12 which supplies clean air to flow through chamber 11. Chamber 11 is held at all times at a slight over-pressure. The measuring chamber 10 has an inlet opening 13 and an outlet 14, and two additional openings 15, 16. Opening 15 forms a light entry opening and opening 16 forms a light exit opening for the measuring chamber 10.

The general construction of the comparison chamber 11 is similar; it has air entry and outlet openings 17, 18 and light entry and outlet openings 19, 20. Disks 21, 22 are located adjacent the openings 15, 16 and 19, 20. Disks 21, 22 are located on a common shaft 23 — shown schematically only — and are rotated by rotation of the shaft 23, driven by a motor (not shown). The flow direction of the gases through chambers 10, 11 is preferably so selected that it corresponds to the direction of rotation of the disks 21, 22. It has additionally been found desirable to so arrange the speed of the disk and the flow speed of the gases through the chambers, particularly of the gas to be measured, that it corresponds to the linear speed of the disks as they pass the measuring chamber. It is also desirable to maintain the temperature of the measuring chamber 10 approximately uniform throughout its length. A resistance wire — not further shown in the drawings — can be introduced into the chamber, the current flow through which is controlled by suitable thermocouples. Neither the resistance wire, nor the heat control devices are shown in the drawings; keeping the average temperature of the measuring gas at a uniform level and matching the speed and direction of movement of disks 21, 22 to the flow speed of the gases increases the accuracy of measurement and further decreases the contamination deposited on disks 21, 22. The measuring chamber 10 is further provided with guide vanes 24, which may be constructed of sheet metal, to provide for uniform distribution of flow of the measuring gas through the measuring chamber.

A light source 25 provides a beam of light which is deflected by mirrors 26, 27 through the measuring chamber 10 as well as through the comparison chamber 11.

An optical lens system 29 to collimate the light beam is located in the measuring beam; an optical lens system 29', corresponding to lens system 29, is located in the comparison beam. Light source 25 preferably provides light at a predetermined color temperature.

Disk 21 is composed of light blocking, or opaque sectors 31 and light-transmissive sectors 32. The opaque and transparent sectors are joined to each other and so located that when an opaque sector 31 is adjacent openings 15, 16 of the measuring chamber, an opaque sector 32 will be adjacent the openings 19, 20 of the comparison chamber. The exact distribution of opaque and transparent sectors of the disk 21 (and similarly of disk 22) is so selected that upon rotation of the disks, the sum of the light passing through the two chambers 10, 11 remains constant when both chambers are filled with clear air.

A collecting lens system 33 is located behind the outlet of measuring chamber 10, followed by a diaphragm 34 to eliminate stray or scattered light; similarly, a lens system 33' is located behind the openings 20 followed, likewise, by a diaphragm 34'. Light guides 35, 36 are located behind the diaphragms 34, 34', guiding the received light to an optical-electrical transducer or sensor 37. Sensor 37 is preferably so constructed that its color sensitivity is matched to the color sensitivity of the human eye, for example due to its inherent composition, or by the use of suitable filters placed between the outlet of the light guides 35, 36 and transducer 37; such filters are not shown.

Operation: Light source 25 emits light which is collimated by the lens system 29, 29', respectively, and guides the light to the respective measuring chamber 10, 11. If an opaque sector 31 is in advance of opening 15 of measuring chamber 10, then light cannot pass through the measuring chamber; rather, deflection mirror 27, polarization filter 30 and lens 20' will guide the light to the comparison chamber 11, through the transparent sector 32 of disk 12 into the comparison chamber and through opening 20 and through the transparent disk 22. Light emitted from opening 20 is guided over the lens system 33', diaphragm 34' and light guide 36 to the light-sensitive surface of transducer 37, which provides a corresponding output signal.

Upon further rotation of disks 21, 22, an opaque sector 31 will reach the opening 19 of the comparison chamber 11, and a transparent sector 32 will reach the opening 15 of measuring chamber 10. Light is now blocked from passing through the comparison chamber 11, but is guided through measuring chamber 10, taking its path through interference filter 28, lens 29, openings 15, 16 and lens systems 33, 34, light guide 35, to sensor 37. The output signal of sensor 37 will be decreased with respect to the output signal previously obtained when light passed through the measuring chamber 11 in dependence on the attenuation of the light beam passing through the measuring chamber due to clouding of the gases in chamber 10. The difference in the output signal from the sensor 37 with respect to the previously measured value is a function of the decreased in optical transmissivity, that is, the contamination of the gases.

The output signal from sensor 37 is amplified in an amplifier A, and the amplified output indicated on an indicator I.

Gas flow along the disks 21, 22 is essentially linear; in spite of the laminar boundary layer which occurs at the surfaces of disks 21, 22, carbon and soot particles, remnants of Diesel oil, or the like, or other contaminating substances (depending on the gas to be measured) may deposit on the disks 21, 22; these deposits will result in a constant decrease in light transmissivity of the disks, and thus cause erroneous measuring results.

Figure 2:
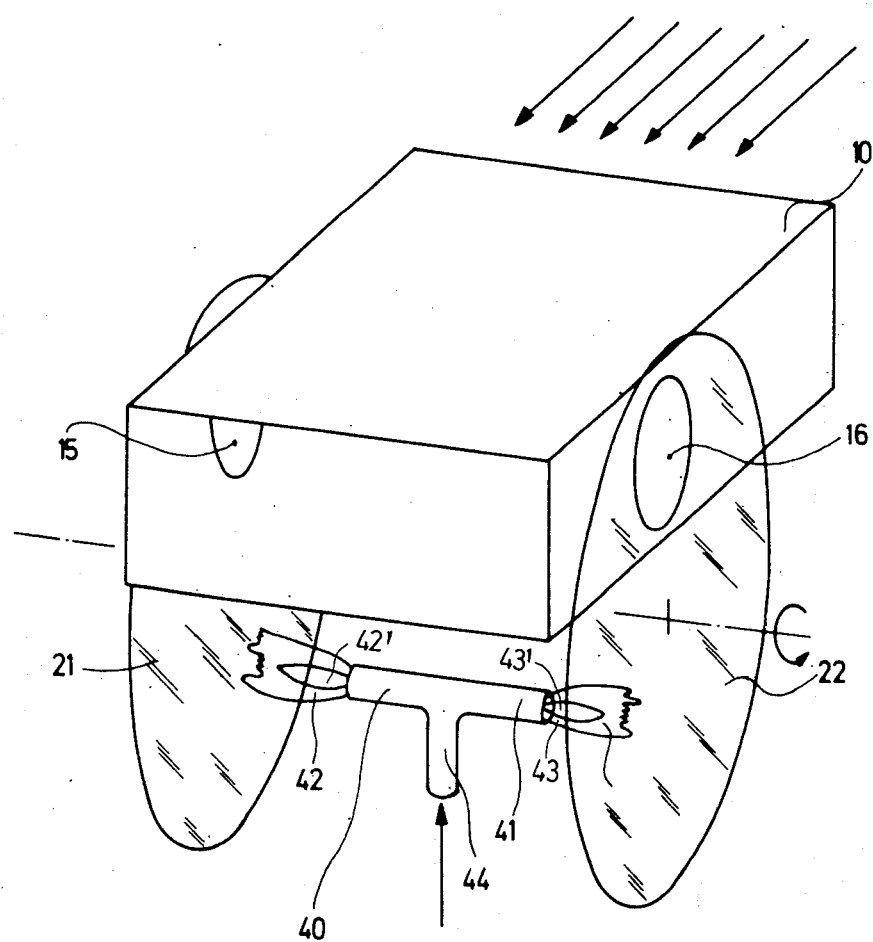
FIG. 2 is a schematic arrangement illustrating the location of gas jet burners adjacent confining disks.

In accordance with the present invention, contaminating components of the exhaust gases which may adhere to the disks are continously and easily removed by burning them off the surfaces of the disks. In accordance with an embodiment of the invention, two gas burners 40, 41 are located in the vicinity of the disks 21, 22. These burners 40, 41 (see particularly FIG. 2) are preferably operated with a highly volatile gas, such as hydrogen, propane, natural gas, coal gas, butane, or methane, or the like. The nature of the burner itself is not critical; electrical heaters, infrared radiators shortware radiation, or micro-wave oven or radiation may be used if the temperature obtained at the surface of the disks is sufficient so that the flash or burn-off temperature of the deposits, typically soot, is reached.

Burners 40, 41 (FIG. 2) are supplied by gas from a supply line 44. The burners are so located and spaced with respect to disks 21, 22, and are so adjusted that flames 42, 43 impinge on the disks with their oxidizing portion, that is, the forward portion of the flames. The reducing, or inner portion 42', 43' of the flames is located in advance of the disks 21, 22.

The size and number of the burners, or of the flames respectively will depend on the size of the disk surface which is to be cleaned which, in turn, depends on the size of the openings 15, 16 respectively. In a preferred form, burners 40, 41 are connected to an automatic ignition and safety shut-off system which, by and itself, is known.

Cleaning of the disks 21, 22 by burninng off deposits thereon has these advantages: The disks 21, 22 are continuously cleaned, so that measuring results will not be subject to erroneous, stray influences. The disks 21, 22, which are rotating, are rapidly brought to an elevated temperature, so that the disks themselves will be less subject to deposit of contaminating substances since exhaust gases will not condense on the disk surfaces.

Figure 3:
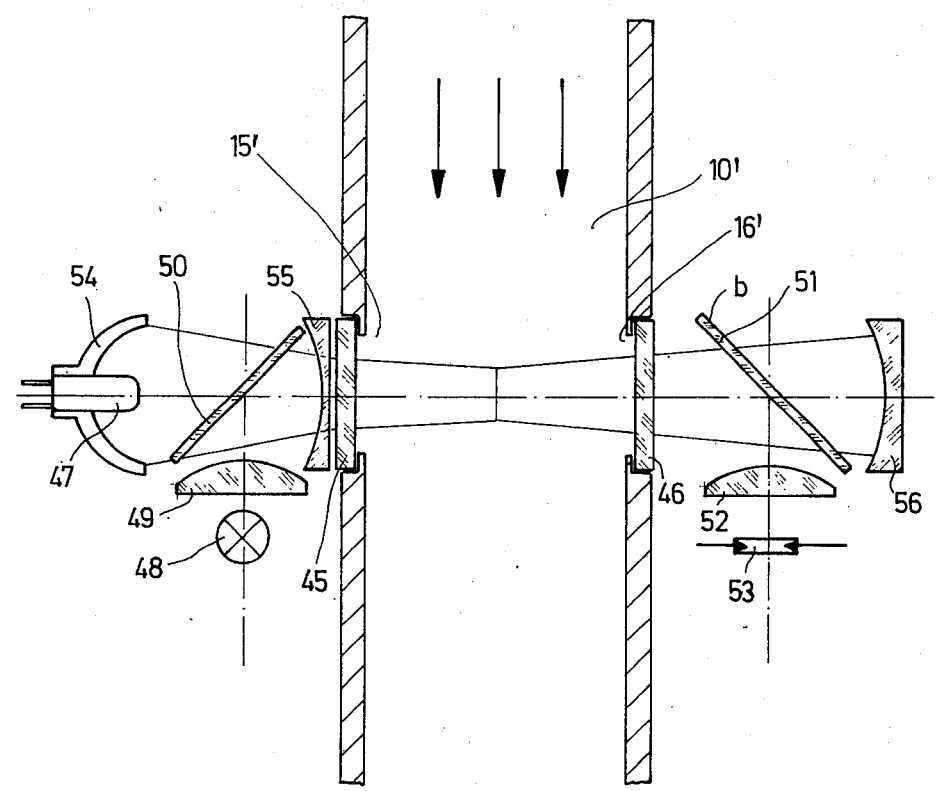
FIG. 3 is a schematic view, in longitudinal cross section, illustrating cleaning of confining transparent walls by means of an electrical burner.

Heating of the disks may be carried out in various ways. Referring to FIG. 3, which illustrates, schematically, an electrical burner: The measuring chamber 10' is shown to an enlarged scale, with its light entry and exit openings 15, 16, which openings are covered by disks 21, 22, which rotate, similar to the embodiment illustrated in connection with FIGS. 1 and 2. Alternatively, fixed cover panes 45, 46 may be set in openings 15', 16' formed in the chamber, as illustrated in FIG. 3. Upon filling chamber 10' with a measuring gas, soot particles or the like may deposit on the panes 45, 46, which soot particles are to be burned off.

To heat the panes 45, 46, an infrared light source 47 is provided which is located to be coaxial to the measuring light beam derived from source 48, the direction of which is indicated in chain-dotted lines. The measuring light beam is applied through a lens 49 to a semi-transparent deflection mirror 50. Deflection mirror 50 deflects the light beam through the measuring chamber, and permits passage of infrared radiation. After the light beam passes through the measuring chamber 10', it is again deflected by a mirror 51 through a lens 52 and applied to a sensor 53, the electrical output of which is characteristic for change in light transmissivity of the gases in chamber 10'.

The deflection mirror 50 is so coated with an interference layer that visible light derived from the light source 48 is deflected by 45°, but permits straight passage of infrared radiation through the mirror 50 without deflection. Thus, infrared radiation from source 47 is directly applied to the covering disk 45. The infrared source 47 is preferably focused and located within a infrared reflector 54.

Since the infrared radiation will spread behind the cover disk 45, the intensity of radiation, that is, the density of infrared radiation may not be sufficient any more to also burn off soot deposits from cover disk 46. In order to burn off soot deposits from cover disk 46, therefore, an infrared source must be located also at the other side of the measuring disk. Power consumption required for a second infrared source, which would duplicate the one on the left side of the disk, can be eliminated if a lens 55 is provided which forms an image of the infrared light source 47 approximately the same density of radiation is imaged on the cover pane 46 as was applied to the cover pane 45. Lens 55 can be located, as shown, either in advance of pane 45 or, alternatively, it may itself form the cover pane. After radiation has passed through the cover pane 45 (formed flat or as a lens) and has passed through the exit pane 46, it is passed through a mirror 51 which is similar to mirror 50, to impinge on a reflector 56 which reflects the infrared radiation back to pane 46 and through the measuring chamber and back towards the infrared source 47. This multiple reflection is attenuated upon multiple passage through the chamber 10', and through the optical elements. Reflector 56, preferably located beyond pane 46 as seen in FIG. 3, may be concave mirror.

Lens 55 forms a dispersion lens; its effect on the measuring beam must be compensated and it is therefore desirable to place a lens 49 in the path of the measuring beam so that the source 48 (and, if an incandescent lamp, its filament) will be imaged centrally within the measuring chamber 10. The refraction of the lenses 49, 52, which may be similar, should be increased if the lens 55 is used.

Various changes and modifications may be made within the scope of the inventive concept.

We claim:
1. Gas transparency measuring apparatus to determine the optical transmission characteristics of gases by measuring the absorption of a bundled beam of light conducted across the gas stream comprising
   a chamber (10, 10') through which the gas to be measured is being conducted;
   a transparent pane (21, 22) defining at least one sidewall of the chamber, the beam of light being conducted through said transparent pane,
   wherein the improvement comprises
   burner means (40, 41; 47, 54, 56) in heat-transmitting relation to the pane and raising the temperature of the pane to a level sufficient to burn off any deposits derived from the gases and deposited on the pane.

2. Apparatus according to claim 1, wherein two panes (21, 22; 45, 46) are provided, located at opposite sides of the chamber, the beam of light being transmitted through both said panes and said burner means heating both said panes to said temperature.

3. Apparatus to measure to optical characteristics of exhaust gases from internal combustion engines comprising
   the apparatus of claim 1
   wherein the exhaust gases are conducted to the chamber (10, 10') and the temperature to which the pane is raised is sufficient to burn off exhaust gases deposits including carbon and soot which form on the pane.

4. Apparatus according to claim 2, wherein the panes comprise rotating disks (21, 22).

5. Apparatus according to claim 2, wherein a burner (40, 41) is associated with each pane and located in heat-transmitting relation with respect thereto.

6. Apparatus according to claim 1, wherein the burner means (40, 41) comprises a gas burner.

7. Apparatus according to claim 6, wherein the gas burner (40, 41) is spaced from the pane (21, 22), and adjusted so that the oxidizing portion of the flame (42, 43) impinges on the pane.

8. Apparatus according to claim 1, wherein the burner means comprises an electrical burner (47, 54).

9. Apparatus according to claim 1, wherein the burner means comprises an infrared light source (47) and providing and infrared light beam which is coaxial to the beam of light being conducted through said transparent disk to provide a measuring beam.

10. Apparatus according to claim 9, further comprising a deflection mirror (50) located intermediate the infrared source (47), the deflection mirror including an interference layer which is transparent to infrared radiation, but provides for deflection of the beam of light forming the measuring beam, the interference mirror being located outside of the measuring chamber and in light-transmitting relation with respect to the pane (45, 46).

11. Apparatus according to claim 10, wherein two interference mirrors (50, 51) are provided, each one located at either side of the chamber, the chamber being bounded by two aligned panes (45, 46), and a reflector (56) is located at the side of the chamber opposite the side at which the infrared source (47) is located to reflect infrared radiation from said source (47) back towards the chamber to the confining panes (45, 46), said second interference mirror (51) conducting measuring light to a measuring means (53).

12. Apparatus according to claim 10, further comprising lens means (55) imaging the infrared radiation source to a point approximately centrally within the measuring chamber (10').

13. Apparatus according to claim 12, wherein the pane (45) and the lens means (55) comprise a unitary element.

14. In the art of measuring the optical transmissivity of gases, having a measuring chamber formed with an opening therein to permit the passage of a beam of light there-through, and transparent cover means closing off said opening,
   the method to prevent contaminating deposits from accumulating on said cover means comprising the step of burning off deposits on the transparent cover means resulting from passage of the gases through the chamber by raising the temperature of said transparent cover means at least at the surface facing the chamber to a temperature sufficient to burn off said deposits.

15. Method according to claim 14, wherein the step of burning off deposits comprises moving the cover means away from the chamber, and subjecting the cover means to an oxidizing flame.

16. Method according to claim 14, wherein the step of burning off deposits comprises applying collimated infrared radiation to said cover means, said radiation having an intensity sufficient to raise the temperature of said cover means to burn off deposits thereon.

17. Method according to claim 14 in which the gases in the measuring chamber for measuring their optical transmissivity characteristics are exhaust gases from an internal combustion engine, particularly from a Diesel engine.

* * * * *